US00PP36112P2

(12) United States Plant Patent
Gasic et al.

(10) Patent No.: US PP36,112 P2
(45) Date of Patent: Sep. 17, 2024

(54) PEACH TREE NAMED EveRes Ruby

(50) Latin Name: *Prunus persica*
Varietal Denomination: EveRes Ruby

(71) Applicant: CLEMSON UNIVERSITY RESEARCH FOUNDATION, Clemson, SC (US)

(72) Inventors: Ksenija Gasic, Clemson, SC (US); Ralph Burrell, Central, SC (US)

(73) Assignee: Clemson University Research Foundation, Clemson, SC (US)

( * ) Notice: Subject to any disclaimer, the term of this patent is extended or adjusted under 35 U.S.C. 154(b) by 0 days.

(21) Appl. No.: 18/445,245

(22) Filed: Jun. 15, 2023

(51) Int. Cl.
*A01H 5/08* (2018.01)
*A01H 6/74* (2018.01)

(52) U.S. Cl.
USPC ..... Plt./197
CPC ..... *A01H 6/7463* (2018.05)

(58) Field of Classification Search
USPC ..... Plt./197
CPC ..... A01H 6/7463; A01H 5/08
See application file for complete search history.

(56) References Cited

PUBLICATIONS

Gasic, Ksenija "Glimpse into the future: New selections from Clemson peach breeding program", 2021 South East Regional Virtual Fruit and Vegetable Conference, Jan. 2021, 30 pages.
Gasic et al "Promising selections and upcoming releases from the Clemson breeding program", 2023 SE Regional Fruit and Vegetable Conference, Jan. 2023, 34 pages.
Gasic, Ksenija "Glimpse into the future: New selections from the Clemson peach breeding program", Jan. 26, 2021, 24 pages.
Gasic et al. "Promising selections and upcoming releases from the Clemson breeding program", Jan. 26, 2023, 19 pages.
Gasic, Ksenija "Developing New Peach Cultivars for the Eastern U.S.", 2021 Mid-Atlantic Fruit and Vegetable Convention, Feb. 10, 2021, 37 pages.
"Advanced Selections In Replicated Trials", Clemson University Peach Breeding Program, Feb. 15, 2022, 17 pages.
Gasic, Ksenija "Clemson Peach Breeding Program", Michigan Spring Peach Meeting, Mar. 10, 2021, 33 pages.
Gasic, Ksenija "Peach Breeding Update", Peach session 2, Mar. 4, 2021, 36 pages.
Gasic et al. "Promising selections and upcoming release from the Clemson breeding program", 2023 Upstate peach grower meeting, Feb. 9, 2023, 21 pages.
Coneva et al. "Performance of Bacterial Spot Tolerant Advanced Peach Selections In Alabama", Jul. 2022, 1 page.
"Peach Breeding at Clemson University: 10 Year of Progress", Southeast Regional Fair Conference, Jan. 22, 2019, 22 pages.
Coneva et al. "Performance of Bacterial Spot Tolerant Advanced Peach Selections In Alabama", Jan. 2023, 1 page.
"Peach Breeding at Clemson University: 10 Years of Progress", Jan. 22, 2019, 22 pages.
Okie et al. "BY520-9, A Peach Rootstock for the Southeastern United States that Increases Scion Longevity", HortScience 29 (6), 1994, pp. 705-706.

*Primary Examiner* — Keith O. Robinson
(74) *Attorney, Agent, or Firm* — Fredrikson & Byron, P.A.

(57) ABSTRACT

A new and distinct variety of peach tree (*Prunus persica*) denominated 'EveRes Ruby' can be distinguished by its firm fruit with slow softening, but eventually melting yellow flesh, early to mid ripening season, large size, attractive appearance, high red skin color, excellent fruit quality, good flavor, and fruit resistance to bacterial spot disease.

3 Drawing Sheets

Latin name of the genus and species of the plant: *Prunus persica.*

Variety denomination: 'EveRes Ruby'.

BACKGROUND

A new and distinct peach cultivar named 'EveRes Ruby' is described herein. The new cultivar originated from open-pollinated seeds of 'Rubyprince' (not patented) peach in 2010 near Seneca, SC. This new cultivar was selected in 2013 for its potential as a fresh-market peach in South Carolina and southern United States. The presently disclosed variety exhibited the outstanding desirable fruit characteristics described below.

Seneca, SC is under a humid subtropical climate. Winters are short and mild with little to no snow, and summers are long, hot, and humid. There is significant annual rainfall averaging 1339 mm (52.7 in) coming from an average of 116 rainy days a year. July has the greatest amount of rainy days (13.8 days), mostly from thunderstorms, with an average of 88.9 mm (3.5 in) rainfall, and rarely exceeding 175 mm (6.9 in) or falling below 33 mm (1.3 in). The average high temperature in the warmest month, also July, is 32° C., with an average heat index at 40° C. The average low temperature in the coldest month, January, is 0.8° C. The hours below 7° C. varies greatly year to year, however, range between 700-1200 hours.

The original plant selection was propagated asexually by budding onto standard peach rootstock cultivar Guardian® (not patented) and a test plot of two plants was established in Seneca, SC. Subsequently, larger test plantings were established with asexually multiplied plants at two additional locations in South Carolina (near Ridge Springs, SC). At each location, propagation was by budding onto the standard peach rootstock cultivar Guardian® (not patented) from buds collected at the test plot in Seneca, SC. No incompatibility or change of scion attributes with Guardian® (not patented) peach rootstocks have occurred following budding. During all asexual multiplication, the characteristics of the original plant have been maintained and no aberrant phenotypes have appeared. The asexual multiplication demonstrates that such reproduction of the characteristics of the tree are consistent and are established or transmitted through succeeding generations.

BRIEF SUMMARY

The new and distinct peach cultivar originated from an open-pollination of 'Rubyprince' in 2010 near Seneca, SC. The seeds collected from the mother tree were germinated in a greenhouse in the late winter 2010/early spring of 2011 and planted in a test field in Seneca, SC. The seedlings fruited during the summer of 2013 and one peach seedling, designated SC10-21-001 was selected for its crisp melting flesh, early to mid-season ripening, attractive appearance, large size, high red skin color, excellent classic peach flavor, postharvest performance, and tolerance to bacterial spot disease. The new cultivar, designated originally as SC10-21-001, tested as SC1, was subsequently named 'EveRes Ruby'.

The claimed variety differs from its parent, 'Rubyprince' (not patented), in that 'EveRes Ruby' is ripening 5-10 days later, around June 15-25 in Seneca, SC, and has low percentage of fruit with pit split. The 'EveRes Ruby' fruit has superior fruit weight and diameter, at 213 g and 75 mm, respectively, compared to 144 g and 60 mm for 'Rubyprince' (not patented). Fruit is further different than the seed parent 'Rubyprince' (not patented) by holding firm on the tree for 10-15 days after shipping ripe. 'EveRes Ruby' fruit flesh is slow softening and requires exposure to room temperature to soften which is different from seed parent 'Rubyprince' fast melting flesh. 'EveRes Ruby' has superior keeping and handling fruit characteristics than seed parent 'Rubyprince' (not patented) as it can be stored up to four weeks at 0° C. without loss of quality or post-harvest decay. The present variety of peach tree when compared to seed parent 'Rubyprince' (not patented) is similar in flavor and eating quality, and has higher tolerance to bacterial spot [*Xanthomonas campestris* pv. *pruni* (Smith) Dye] in fruit.

BRIEF DESCRIPTION OF THE DRAWINGS

The accompanying photographs show typical specimens of the new cultivar in color as nearly true as it is reasonably possible to make in a color illustration of this character.

DETAILED BOTANICAL DESCRIPTION

Figure 1:
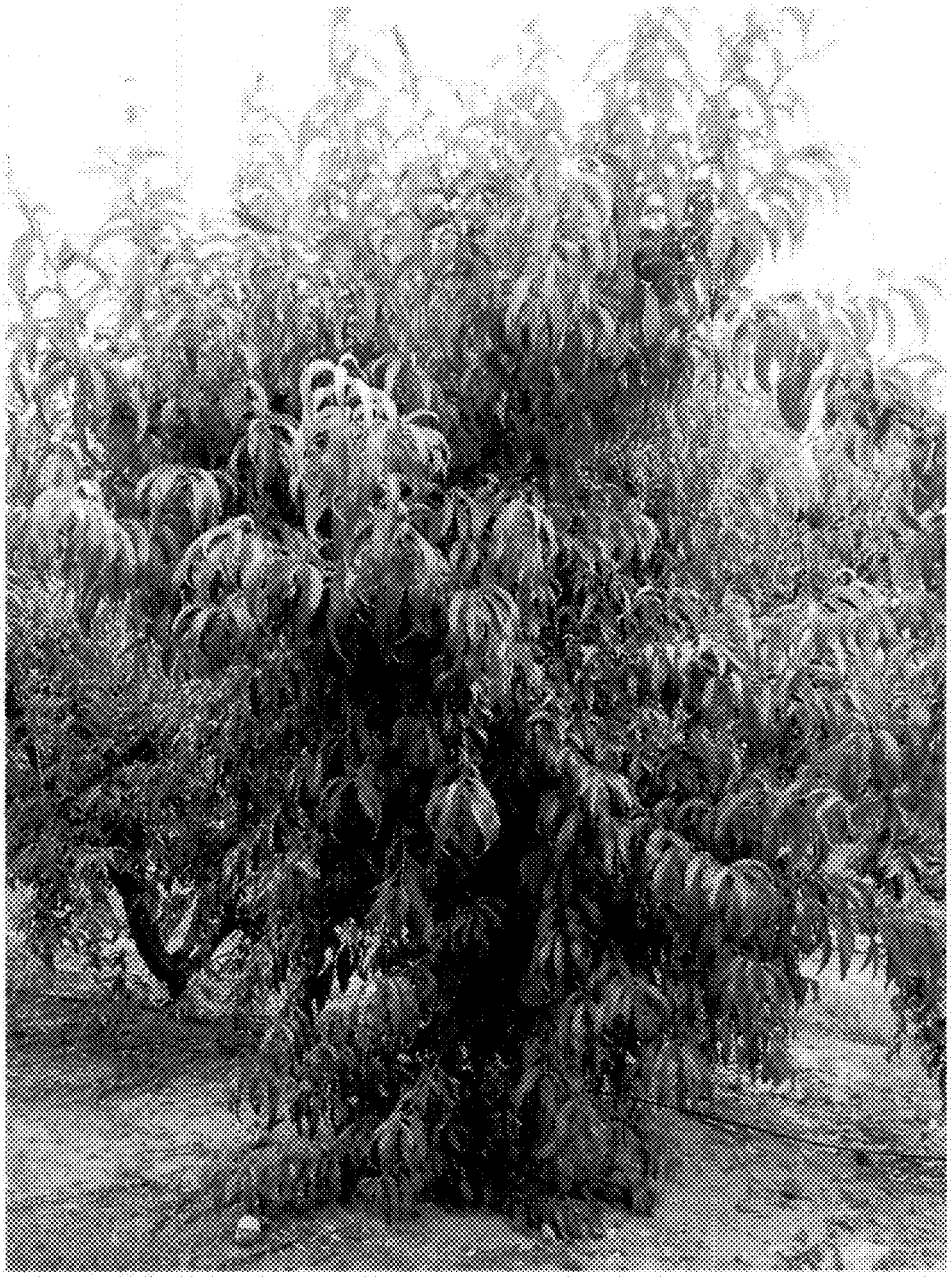
FIG. 1 is a photograph of mature fruit on a tree of 'EveRes Ruby' at ten years of age.
Figure 2:
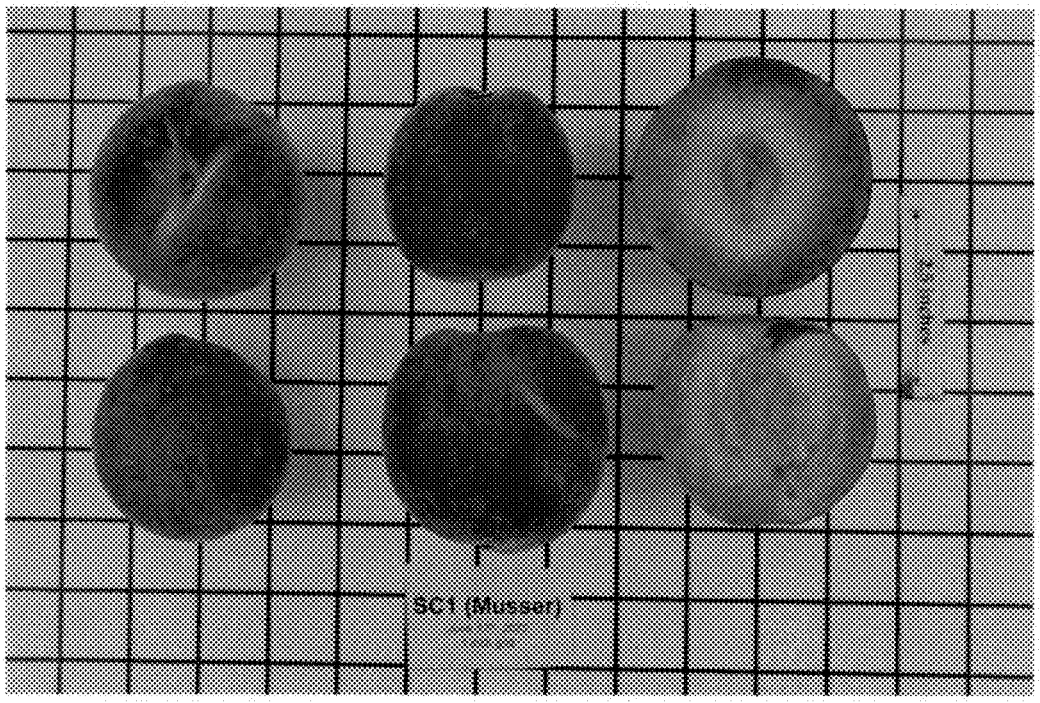
FIG. 2 is a photograph of a whole and longitudinally cut fruit of 'EveRes Ruby' at maturity at ten years of age.
Figure 3:
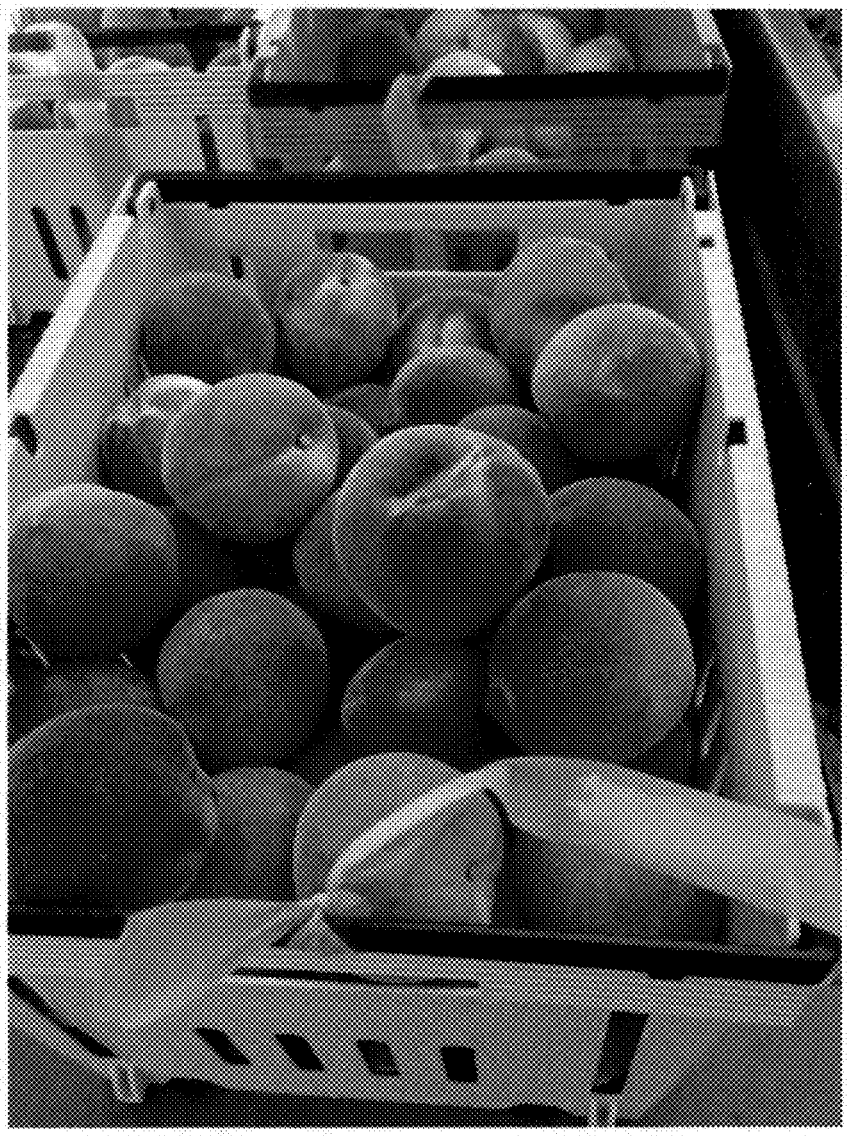
FIG. 3 is a photograph of harvested mature 'EveRes Ruby' fruit at ten years of age.

Plants and fruit of this new cultivar differ phenotypically from its parent. While 'EveRes Ruby' has yellow and melting flesh, textured like its parent ('Rubyprince'), 'EveRes Ruby' fruit has superior firmness and size than 'Rubyprince' (not patented) and ripens 5-10 days later. 'EveRes Ruby' fruit has superior keeping and handling quality compared to the seed parent 'Rubyrince' (not patented) as it hangs longer on the tree after shipping ripe, allowing delayed and compressed harvest, and requires exposure to room temperature for flesh to soften. 'EveRes Ruby' has a high tolerance to fruit infection from bacterial spot.

Trees of the new cultivar are moderately vigorous, productive, standard in size, well-branched and symmetrical with an upright to semi-spreading growth habit, comparable to other peach and nectarine trees. Trees express a high level of tolerance to both foliar and fruit infection of bacterial spot [*Xanthomonas campestris* pv. *pruni* (Smith) Dye]. The new cultivar blooms in the spring around the middle of March, which is between the early to middle range of all cultivars blooming in Seneca, SC. No winter cold injury has been observed on wood or buds of the new cultivar in South Carolina tests where minimum temperatures have reached 5° F. (−15° C.) during evaluation. Bud chill hardiness ranges from −15 to −20° C. Chilling requirement to break dormancy is estimated to be 45-50 chill portions or 800 chill hours below 45° F. (7° C.).

Fruit of the new cultivar ripens early to mid-season, averaging 2-3 days before 'Summerprince' (not patented, used as a check) and 5-10 days after 'Rubyprince' (not patented). Average first ripening date is June 15 in upstate South Carolina (Seneca). Very few split pits, averaging only 3% of total pack out volume. Fruit yields have been good with an estimated 78.97 kg total yield on $4^{th}$ leaf, open center trees.

The fruit is round in shape. Fruits are attractive with an average 95% dark red blush (Greyed-Purple Group, 185A). The fruit skin has light pubescence. The flesh of the fruit is yellow in base color with red pigments and flecking. Flesh is of the melting type but is very crunchy and firm at maturity. The fruit is a clingstone, in that the flesh adheres to the pit. Fruit size is large, averaging 179 g. The fresh fruit has excellent classic peach flavor and was rated highly in evaluations. Fruits average 11.2% soluble solids, but flavor is sweet and well balanced with moderate acidity. The acidity level of 'EveRes Ruby' was 0.65% malic acid.

The following is a detailed description of the botanical and pomological characteristics of the subject peach. Color data are presented in Royal Horticultural Society Colour Chart designations (2015 $6^{th}$ revised edition). Where dimensions, sizes, colors and other characteristics are given, it is to be understood that such characteristics are approximations of averages set forth as accurately as practical.

Plants used for botanical data were at their $4^{th}$ leaf and grown on berms on a fine sandy loam soil with stake irrigation near Clemson, SC. Trees were trained to an open-center training system and dormant pruned annually. Fruits on all trees were thinned to approximately 6 inches between fruits 4-5 weeks after full bloom. The trees were fertilized near budbreak (late March on average) with 19-19-19 fertilizer. Weeds were controlled with pre- and postemergence herbicides. Routine commercial fungicide and insecticide applications were made to the trees. The descriptions reported herein are from specimens grown near Clemson, SC.

Plant:

*Size*.—Mature trees ($4^{th}$ leaf) average 2.59 m in height and 3.35 m in spread or width, and a semi-upright growth habit, as grown on Guardian® (not patented) rootstock using an open-center training system commonly used on peaches.

*Growth*.—Vigorous, symmetrical form, good canopy development.

*Productivity*.—Good productivity and consistent from year to year. High bud density, and fruit set. Yields averaged 72.31 kg/tree for 'EveRes Ruby' greater than 'Rubyprince' (not patented) at 67.14 kg/tree and similar to 'Summerprince' (not patented) at 76.1 kg/tree.

*Cold hardiness*.—Wood and dormant buds hardy to 5° F. (−15° C.). This was the coldest temperature that the trees were exposed to at the test site, but hardiness may exceed this temperature.

*Disease resistance*.—Leaves and fruit tolerant but not immune to bacterial spot under growing conditions where bacterial spot infection is often very severe on susceptible genotypes. A commercial fungicide program was utilized in orchards used in the development and evaluation of the instant cultivar, thus, no resistance to brown rot (*Monilinia fructicola* (G. Winter) Honey) or scab (*Fusicladium carpophilum* (Thum.) Oudem), or to the other common diseases at Clemson, SC, were determined.

*Insect resistance*.—Insecticides were applied to orchards used in the development of the instant cultivar to control the common insects at the location including oriental fruit moth (*Grapholita molesta* (Busck)), plum curculio (*Conotrachelus nenuphar* (Herbst)), stinkbug (*Halyomorpha halys* (Stal); *Euschistus servus* (Say); *Acrosternum hilare* (Say); *Nezara viridula* (Linnaeus); *Thyanta* spp.), tarnished plant bug (*Lygus lineolaris* (Palisot de Beauvois)), lesser peach tree borer (Synathedon pictipes (Grote & Robinson)), and greater peach tree borer (*Synanthedon exitiosa* (Say)). Therefore, no insect resistance was determined in the testing of the instant cultivar.

Foliage/shoots/branches:

*Shoots*.—Smooth. Dormant-season shoot; Dormant-season shoot color top: Greyed Purple Group 187-A; bottom: Green Group 143C. Mature shoot internode length: base 3.4 cm, midpoint 2.3 cm, terminal 1.0 cm. Mature shoot internode diameter: base 5.6 cm, midpoint 4.0 cm, apex 3.4 cm.

*Branches*.—Length 47.75 cm; diameter at base 0.475 cm; diameter at midpoint 0.35 cm; diameter at terminal 0.2 cm.

Leaves: Simple, alternate, glabrous, lanceolate, petiolate, and deciduous. Venation pinnate; base acute; terminal or apex acuminate; margin serrated. Mature leaf size: length 16.4 cm; width midpoint 3.8 cm. Leaf serrations 4.4 cm. Mature leaf color: abaxial—Moderate Olive Green (147B); adaxial—Grayish Olive green (NN137B). Young leaf color: abaxial—Moderate Yellow Green (146B); adaxial—Strong Yellow Green (144A); Petiole length—mature leaf: 0.96 cm, petiole width: 2.2 mm; petiole texture: smooth no pubescence; petiole strength: average to strong. Leaf glands: reniform, average of 1.6 per leaf, located at base of leaf blade at top of petiole. Leaf glands are 0.12 cm in lenght and 0.25 mm in diameter. Stipule length: 1.3 mm. width: 0.5 mm.

Buds: Number of leaf buds per 15 cm: 6.4, evenly distributed along the shoot. Number of flower buds per 15 cm from terminal: 11.6.

Bark (of mature trunk of tree):

*Color*.—Dark Greyish Yellowish Brown (N199B).

*Texture*.—Rough.

Trunk:

*Diameter*.—11.43 cm (at 25 cm above ground level).

Flower buds: Dormant flower bud length 0.5 cm and diameter 0.25 cm and color Red Purple Group (59A); dormant buds swell and expand in late winter and increase in size during this expansion to fully open flowers.

Flowers: Bloom occurs prior to vegetative bud break; solitary to occasional double individual flowers at a single node; perfect; self-fertile.

*Date of bloom*.—50%, Julian 70 (March 11); 90%, Julian 73 (March 14) which is early to middle bloom period for all cultivars in Seneca, SC; 'Rubyprince' (not patented) 90%, Julian 74 (March 15).

*Size*.—Diameter fully open 3.02 cm.

*Type*.—Showy.

*Color*.—Adaxial/abaxial: Deep Pink 185-D/ Dark Purplish Pink — 186-C.

*Petals per flower*.—5; length 20.4 mm; width 12.8 mm; texture smooth; shape teardrop.

*Length of pistil*.—1.6 cm; positioned below anthers.

*Width of pistil*.—1 mm.

*Stamens*.—Average 39.2/flower with pollen present, fertile and abundant.

*Ovary*.—Pubescence, round to oval. Grayed-Green Group (193A).

Fruit:

*Size*.—Large, avg. 213 g; diameter 75 mm. Diameter stem end 6.6 cm, equator 7.6 cm, blossom end 6.3 cm; length base to apex 7.6 cm.

*Shape*.—Round, symmetrical with no tip.

*Skin*.—Light pubescence, attractive; ground color Grayed-Orange Group N172 B with red blush (Grayed-Purple Group 187A) covering about 95% of surface on average. Becomes deep red blush (Greyed-Purple Group 185A) around a week before commercially ripe.

*Flesh*.—Color Yellow Group (12C); clingstone; uniform slow softening, melting texture. Firmness 4.89 $kg/cm^2$. Commercially ripe it is crunchy and firm, but has excellent eating quality once it softens, usually after 2-3 days at room temperature; classic peach flavor, sweet, and moderate acid.

*Pedicel length*.—0.9 cm.

*Pedicel diameter*.—0.4 cm.

*Pedicel color*.—Green Group 143C.

*Pedicel strength*.—Strong; holds on well.

*Ripe date*.—June 15 (Julian 156) in upstate South Carolina; 'Rubyprince' (not patented) ripens June 11 (Julian 152). Fruit development period Julian 83; 'Rubyprince' (not patented) Julian 86. Ripening of individual fruit is uniform. Extremely slow softening and can sit on the tree for a month without softening.

*Tendency of pit to split*.—Light splitting, around 3% of total pack out. Less splitting than 'Rubyprince'.

*Soluble solids*.—11.2%.

*Fruit juice pH*.—3.35.

*Fruit juice titratable acidity*.—0.65% malic acid.

*Fruit glossiness*.—Weak.

*Storage performance*.—Overall for 0-3 weeks of storage 'EveRes Ruby' peforms well and shows no loss in fruit quality.

Pit/stone:

*Size*.—Length 3.8 cm; diameter (midpoint) 2.6 cm.

*Shape*.—Oblong, truncate base, unequal side, furrowing and pitting.

*Color*.—Red-Purple (59C) when flesh freshly cut.

Kernel:

*Size*.—Length 2.2 cm; diameter 1.28 cm.

*Shape*.—Ovate with acute tip and obtuse base.

*Color*.—Yellow Orange (16C).

Uses: Fresh consumption, not evaluated for drying or other uses.

The cultivar: The outstanding characteristics of 'EveRes Ruby' are attractive appearance, longevity on tree without softening, yellow fleshed peach, crisp texture, postharvest storage potential, and bacterial spot tolerance. 'EveRes Ruby' stands out from other cultivars due to extremely high pack out volume, size consistency, firmness, and excellent eating quality.

The invention claimed is:

1. A new and distinct cultivar of peach tree named 'EveRes Ruby,' substantially as illustrated and described herein.

* * * * *